US006905675B2

(12) United States Patent
Shacknai et al.

(10) Patent No.: US 6,905,675 B2
(45) Date of Patent: *Jun. 14, 2005

(54) SULFUR CONTAINING DERMATOLOGICAL COMPOSITIONS AND METHODS FOR REDUCING MALODORS IN DERMATOLOGICAL COMPOSITIONS

(75) Inventors: Jonah Shacknai, Scottsdale, AZ (US); Eugene H. Gans, Phoenix, AZ (US); Ray Figureoa, Medley, FL (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/283,102

(22) Filed: Oct. 29, 2002

(65) Prior Publication Data

US 2004/0057972 A2 Mar. 25, 2004

Related U.S. Application Data

(63) Continuation of application No. 09/607,881, filed on Jun. 30, 2000, now Pat. No. 6,514,489.

(51) Int. Cl.[7] .......................... A61K 7/42; A61K 33/04
(52) U.S. Cl. .................. 424/70.1; 424/401; 424/703; 424/705; 424/706; 514/613; 514/886; 514/887
(58) Field of Search ................ 424/70.1, 401, 424/703, 705, 706; 514/613, 886, 887

(56) References Cited

U.S. PATENT DOCUMENTS

| | | |
|---|---|---|
| 3,634,264 A | 1/1972 | Pence |
| 4,388,301 A | 6/1983 | Klein |
| 4,587,123 A | 5/1986 | Price |
| 4,752,472 A | 6/1988 | Kligman |
| 5,344,971 A | 9/1994 | Dedieu et al. |
| 6,429,231 B1 | 8/2002 | Bhagwat et al. |
| 6,514,489 B1 * | 2/2003 | Shacknai et al. .......... 424/70.1 |

FOREIGN PATENT DOCUMENTS

| | | |
|---|---|---|
| EP | 0 576 287 A1 | 12/1993 |
| JP | 03-002124 | 1/1991 |
| WO | WO 82/04393 A1 | 12/1982 |
| WO | WO 92/05764 | 4/1992 |
| WO | WO 98/04241 A2 | 2/1998 |
| WO | WO 98/47466 A3 | 10/1998 |
| WO | WO 99/24003 A1 | 5/1999 |

OTHER PUBLICATIONS

Harry, R.G., *Harry's Cosmeticology*, pp. 558–561, 6th edition (1973).
Bonnar, et al., "The Demodex Mite Population in Rosacea," Journal of the American Academy of Dermatology, vol. 28, No. 3, Mar. 1993, p. 443–448.
Diaz–Perez, et al., "Demodex mites in Rosacea" and "Reply," Journal of the American Academy of Dermatology, vol. 30, No. 5, Part I, May 1994, p. 812–813.
"Dermatology in General Medicine," 5th ed., CD–ROM, 1999, Chapter 74 p. 1–16.
Lin, et al., "Sulfur Revisited," Journal of the American Academy of Dermatology, vol. 18. No. 3, Mar. 1988, p. 553–558.
Maibach, et al., "Sulfur Revisited," and "Reply," Journal of the American Academy of Dermatology, vol. 23, No. 1, Jul. 1990, p. 154–156.
The Merck Manual, Seventeenth Edition (1999), pp 811–814.
Marks, "Histopathology of Rosacea", Arch. Derm., vol. 100, Dec. 1969 pp 683–691.

* cited by examiner

Primary Examiner—Jyothsna Venkat
(74) Attorney, Agent, or Firm—ReedSmith LLP; William J. McNichol, Jr.; Maryellen Feehery

(57) ABSTRACT

A method for reducing the production of malodor in sulfur containing dermatological compositions by adjusting the pH of the composition to between about 6.5 to about 8.1. Also, sulfur containing dermatological compositions having a pH between about 6.5 and about 8.1.

28 Claims, No Drawings

SULFUR CONTAINING DERMATOLOGICAL COMPOSITIONS AND METHODS FOR REDUCING MALODORS IN DERMATOLOGICAL COMPOSITIONS

This application is a continuation of U.S. patent application Ser. No. 09/607,881, filed Jun. 30, 2000 now U.S. Pat. No. 6,514,489.

FIELD OF THE INVENTION

The present invention relates methods of reducing, inhibiting or eliminating malodor in dermatological compositions containing sulfur. The invention also relates to sulfur containing dermatological compositions that produce little or no malodor.

BACKGROUND OF THE INVENTION

Elemental sulfur (in a variety of forms), sulfides, sulfites and/or mercaptans are commonly used ingredients in der-matologic or cosmetic compositions for the treatment of a variety of dermatological conditions. Various forms of sulfur, sulfides, sulfites and mercaptans are believed to have anti-microbial, anti-fungal, anti-parasitic and anti-inflammatory functions. Sulfur, in its various forms, sulfides, sulfites and mercaptans are believed to kill parasites, such as mites, and microorganisms, including but not limited to bacteria, and thereby also suppress their endotoxins and exotoxins, all of which can be irritants that may contribute to the provocation of itching, redness and irritation that are characteristics of rosacea. Further, sulfur causes keratolytic/sloughing activity and may, therefore, remove irritants that are held by the sloughed cells, as well as smoothing and soothing the skin.

Unfortunately, sulfur containing compositions may be, or may become, malodorous over time yielding a characteristic "rotten egg odor." This malodor is believed to be caused by the formation of volatile sulfur-containing compounds, for example, hydrogen sulfide ($H_2S$), sulfur dioxide ($SO_2$) and various other volatile sulfides and mercaptans. These odor causing compounds can be generated even by sulfur compounds which are not themselves odor causing. As a result of the unpleasant odor, patients are sometimes reluctant to apply such compositions directed by their physician or pharmacist. Such poor patient compliance can seriously diminish the effectiveness of a treatment regimen.

The prior art has used a variety of techniques to try to deal with the odor associated with sulfur containing compositions. For example, U.S. Pat. No. 4,338,301 describes the use of clays to control the odor of alkaline sulfur containing compositions. Another approach to odor content is to include compounds that react ionically or covalently with odor causing sulfur compounds to reduce or eliminate offensive odors. Examples of agents that can tie-up volatile compounds, such as $SO_2$, $H_2S$, —SH compound, sulfur include heavy metal oxide and related compounds such as zinc oxide, titanium oxide that can form non-volatile or weakly volatile sulfides such as Zinc sulfide, or telamursulfide and the like. Other approaches include the use of scents or perfume to overpower or mask the offensive odor. Sometimes, formulators forgo the use of particular sulfur compounds that generate strong odors, even though they are otherwise desirable. None of these techniques have been entirely satisfactory.

Accordingly, there is a need for improved methods for reducing, inhibiting or eliminating the production of sulfurous malodor in sulfur containing dermatological or cosmetic compositions.

SUMMARY OF THE INVENTION

The present invention is directed to a composition comprising a sulfur ingredient and a carrier, wherein the composition has a pH of from about 6.5 to about 8.1. Alternatively, the hydrogen ion concentration of the composition should be no more than $3.16 \times 10^{-7}$ and no less than $7.95 \times 10^{-9}$.

The present invention is also directed to a method for reducing or inhibiting the production of malodor in sulfur containing dermatological compositions comprising the step of adjusting the pH of the composition to between about 6.5 to about 8.1.

The present invention is also directed to a dermatological composition suitable for topical application to human skin, comprising: at least one sulfur ingredient; and a pharmaceutically acceptable carrier, wherein the composition has a pH of about 6.5 to about 8.1 and the composition exhibits substantially reduced sulfur odor, particularly after aging.

DETAILED DESCRIPTION

It has been discovered that the occurrence of sulfur malodor in commercially available sulfur containing dermatological and cosmetic compositions may be reduced, inhibited or eliminated by formulating sulfur containing dermatological compositions to minimize the production of volatile sulfur derivatives, initially and as the composition ages. This may be accomplished by selectively incorporating ingredients that result in the sulfur containing composition having a pH from about 6.0 to 8.5, preferably about 7.0 to about 8.1, or by adding acid or base to the composition to bring the pH of the composition within the desired range. It should be noted that, unlike prior art techniques which call for covalent or ionic bonding with the odor causing sulfur compounds, the present invention does not remove or scavenge odor causing entities, but rather renders them less offensive. It is believed that by avoiding these reactions the effectiveness of the composition is preserved or even enhanced. The present invention is broadly applicable to all types and classes of sulfur containing dermatological and cosmetic compositions, including, for example and without limitation, lotions, masks and cleansers.

The present invention is directed to a composition comprising: at least one sulfur containing ingredient; and a pharmaceutically or cosmetically acceptable carrier, wherein the composition has a pH of from about 6.5 to about 8.1, preferably about 7.0 to about 8.1. The present invention is also directed to a method for reducing or inhibiting initially and over time the production of malodor in sulfur containing dermatological compositions comprising the step of adjusting the pH of the composition to between about 6.5 to about 8.1

Suitable sulfur ingredients are those that are suitable for use in dermatological compositions, including, without limitation, elemental sulfur, sulfides, sulfites and mercaptans and combinations thereof A preferred sulfur compound is sodium sulfacetamide. As used herein, the term "sulfur containing dermatological composition" means any composition that contains elemental sulfur, organic or inorganic sulfides, inorganic sulfites, organic or inorganic mercaptans, or any other and that is used by being applied to the skin or hair of a user.

Forms of elemental sulfur suitable for use in the present invention are those forms of elemental sulfur that are known to be useful in dermatological compositions, including, without limitation, colloidal, coated, enrobed, entrapped, fumed, precipitated, and sublimed sulfur. Elemental sulfur, as that term is used herein, will also be understood by one of ordinary skill in the art to include other transformations, fractions and derivatives of sulfur understood by those of ordinary skill in the art to be useful in dermatological compositions. The preferred form of sulfur for use in the present invention is precipitated sulfur.

Inorganic sulfides suitable for use in connection with the present invention are those inorganic sulfides known to be useful in dermatological compositions and include, without limitation, selenium sulfide, sodium thiosulfate as well as those inorganic sulfides having the formula:

RS;

RSH;

$R_2S$;

RSSR; or

RSSH, wherein

R is an inorganic element that can bind ionically or covalently with sulfur.

Organic sulfides suitable for use in connection with the present invention are those organic sulfides known to be useful in dermatological compositions and include, without limitation, those organic sulfides having the formula:

RS;

$R_2S$;

RSH;

R'SSR', or

R'SSH, wherein

R' is an organic compound and its salts that can bind ionically or covalently with sulfur. Exemplary organic sulfides include, without limitation, sodium thioglycolate (sodium mercaptoacetic acid), gluathione.

Inorganic sulfites suitable for use in the present invention are those inorganic sulfites known to be useful in dermatological compositions, including, without limitation, sulfites and meta bisulfites.

Additional ingredients in these compositions may include, without limitation, solvents, viscosity adjusters compositions, cleansers, propellants, emollients, emulsifiers, moisturizers, preservatives, antioxidants, odor modifiers, fragrances, any other ingredient that might be useful in a dermatologic or cosmetic composition. For example, antimicrobial agents, antifungal agents, anti-inflammatory agents, immunomodulator or immunosuppressant agents, antiparasitic agents, keratinization modulators, depigmenting agents, antihistamines, antioxidants, analgesics, and any other active ingredient suitable for use in dermatological compositions may be used.

It is known by those of ordinary skill in the art how to identify the sets of ingredients necessary to give a dermatological composition its desired physical and esthetic properties. By way of example only, U.S. Pat. No. 4,847,071, which is incorporated herein by reference, includes a detailed discussion of many of the ingredients used in carriers for dermatological compositions and carriers, such as lotions, creams, oils, gels, etc. U.S. Pat. No. 4,847,071 also includes an extensive discussion of cleaning compositions useful in certain dermatological compositions.

The step of adjusting the pH of the composition may be accomplished by selecting particular ingredients that combine to yield a composition having the target pH. In cases where the selection of ingredients yields a sulfur containing dermatological composition that does not have the target pH, it may be adjusted by adding an acid or base to the composition in an amount sufficient to bring the pH of the composition within the target range. Commonly used acid or bases that may be safely incorporated into a dermatological composition may be used for this purpose. Preferred acids include, without limitation, HCl and citric acid. Preferred bases include, without limitation, NaOH and triethanolamine. The acid or base may be added at any appropriate time during the formulation of the sulfur containing composition.

Suitable antimicrobial agents may include any antimicrobial agents useful in dermatological compositions. Suitable antimicrobial agents include, without limitation, benzoyl peroxide, povidone iodine, hexachlorphene, chlorhexidine, mupirocin, gentimycin, neomycin, bacitracin, polymixin, erythromycin, clindamycin, metronidazole, clarithromycin, silver sulfadiazine, dapsone, zinc pyrithione, cephalosporin, thymol, mafenide acetate, nitrofurazone, generators of nitrix oxide benzyl alcohol, sulfamethoxazole, sulfasalazine, sulfasoxazole, acetylsulfasoxazole and combinations thereof. A preferred set of antimicrobial agents consists of hexachlorphene, mupirocin, gentimycin, neomycin, bacitracin, polymixin, erythomycin, clindamycin, metronidazole, clarithromycin, dapsone, cephalosporin, thymol, mafenide acetate, nitrofurazone, benzyl alcohol, sulfamethoxazole, sulfasalazine, sulfasoxazole, and acetylsulfasoxazole.

Suitable antifungal agents may include any antifungal agents useful in dermatological compositions. Suitable antifungal agents include, without limitation, nystatin, ciclopirox and ciclopirox olamine, griseofulvin, itraconazole, fluconazole, ketoconazole, terbinafine, econazole, benzyl alcohol, undecylenic acid and salts thereof, benzyl benzoate and combinations thereof. Preferred antimicrobial agents are ciclopirox and ciclopirox olamine, nystatin, griseofulvin, itraconazole, fluconazole, ketoconazole, terbinafine, econazole, benzyl alcohol, and benzyl benzoate.

Suitable anti-inflammatory agents may include any anti-inflammatory agents useful in dermatological compositions. Suitable anti-inflammatory agents include, without limitation, aldometasone, amcenonide, betamethasone, esters of betamethasone, desonide, clobetasole propionate, clocortolone pivilate, triamcinilone acetonide, desoximetasone, dliforosone, mometosone furoate, prednicarbate, fluocinonide, fluocinolone acetonide, hydrocortisone and combinations thereof.

Suitable immunomodulators or immunosuppressants may include any immunomodulators or immunosuppressants useful in dermatological compositions. Suitable immunomodulators or immunosuppressants include, without limitation, cylclosporine, imiquimod, flurouracil, podophilox, podophyllin, and combinations thereof. Preferred immunomodulators or immunosuppressants consists of cylclosporine, imiquimod, and flurouracil.

Suitable antiparasitic agents may include any antiparasitic agents useful in dermatological compositions. Suitable antiparasitic agents include, without limitation, malathion, pediculosides, scabicides, ivermectin, permethrin, pyrethrin, carbamyl, imiquimod, thiabendazol, and combinations thereof Preferred antiparasitic agents includes consists of pediculosides, scabicides, ivermectin, permethrin, pyrethrin, carbamyl, imiquimod, and thiabenazole.

Suitable keratinzation modulators may include any keratinzation modulators useful in dermatological compositions. Suitable keratinzation modulators include, without limitation, retinol, retinoic acid, retinaldehyde, retinal, retinyl esters, tazarotene and other retinoids, alpha and beta hydroxy acids salicylic acid, resorcinol, retinal esters and combinations thereof. Preferred keratinization modulators are retinol and its derivatives.

Suitable depigmenting agents may include any depigmenting agents useful in dermatological compositions. Suitable depigmenting agents include, without limitation, hydroquinone, monobenzone and azaleic acid, salicylic acid and alpha and beta hydroxy acids, ascorbic acid and ets esters and combinations thereof. Preferred depigmenting agents include hydroquinone, monobenzone and azaleic acid.

Suitable antihistamines may include any antihistamines useful in dermatological compositions such as diphenhydramine.

Suitable antioxidants may include any antioxidants useful in dermatological compositions such as diphenhydramine. Suitable antioxidants include, without limitation, ascorbic acid, its esters and salts and derivatives thereof, vitamins A, D, and K, tocopherol and its derivatives and combinations thereof.

The following terms are recognized in the art to have the following meanings. $Na_2EDTA$ is defined to mean disodium ethylene diamine tetra acetate. BHT is defined to mean butylated hydroxytoluene. MEA is defined to mean monoethanolamine. PEG-100 is defined to mean polyethylene glycol 100.

The step of selecting one or more additional ingredients from the one or more sets of ingredients and combining the selected ingredients to form a sulfur containing dermatological composition having a pH of about 6.5 to about 8.1, preferably about 7.0 to about 8.1 preferably includes the selection of ingredients based on both their functional properties and their pH. That is, in selecting each ingredient consideration should be given not only to the function that a particular ingredient will impart to the composition, but also to what extent the addition of the requisite amount of that ingredient will affect the pH of the sulfur containing dermatological composition. For example, if one desired to select from a particular set a particular ingredient that will make the pH of the sulfur containing dermatological composition lower than the target pH, then, when selecting other ingredient(s) from the same or different set, one should seek to select ingredient(s) that will offset the effect of the first ingredient. In some cases, the selection process may be very simple requiring only, for example, that 2 different ingredients offset one another. In other cases, the selection process may be very complex requiring the simultaneous consideration of the effect on pH of numerous different ingredients and the quantities in which those ingredients are incorporated into the sulfur containing composition. If the selection of ingredients yields a composition that does not have the desired pH, this can be adjusted by adding an acid (such as hydrochlonic or sulfuric acid) or a base (such as sodium hydroxide, potassium hydroxide, or triethlanolamine) in such quantity as will yield the desired pH. Buffers may also be used to help achieve and maintain this result.

The invention will be explained further by a consideration of the following Examples, which are given solely for the purpose of illustration and are not to be construed as limitations of the present invention since many variations thereof are possible without departing from the scope or spirit of the invention.

EXAMPLE 1

A sulfur containing lotion was prepared by combining the components set forth below in accordance with the procedure set forth below.

|  | % by Weight |
|---|---|
| Phase A | |
| Sulfacetamide sodium, USP | 10.50 |
| Xanthan gum | 0.30 |
| Disodium EDTA, NF | 0.10 |
| Sodium thiosulfate | 0.10 |
| Purified water | q.s. |
| Phase B | |
| Light mineral oil, NF | 5.00 |
| Isopropyl myristate | 6.00 |
| Stearyl alcohol, NF | 1.20 |
| Cetyl alcohol, NF | 1.80 |
| Hydrogenated coco-glycerides | 1.30 |
| Benzyl alcohol, NF | 1.00 |
| Zinc ricinoleate | 0.50 |
| Sorbitan stearate | 2.10 |
| Dimethicone, NF | 0.50 |
| Polysorbate 60 | 3.40 |
| Glyceryl stearate and PEG-100 stearate | 0.85 |
| Phase C | |
| Sulfur precipitated, USP | 5.00 |
| Propylene glycol | 8.00 |
| Purified water | 4.00 |
| Phase D | |
| Ordenone | 1.00 |
| Fragrance 27160 | 0.10 |

The water of Phase A was first loaded into a suitable-sized kettle equipped with a Lightnin® type mixer and a double motion impeller. The Lightnin® mixer was started to provide fairly vigorous stirring, the water was heated to about 80–85° C., and the xanthan gum was slowly sprinkled to form a clear, lump-free solution. While the temperature and mixing conditions were maintained, sodium thiosulfate and sodium sulfacetasmide and disodium EDTA were added and were completely dissolved.

Phase B was made in a separate smaller kettle. All of the ingredients of Phase B were added to the kettle and were heated to about 80–85° C. As the solids melt, slow mixing was initiated and continued until all solids were melted.

When both Phase A and Phase B were at about 80–85° C., the mixing speed to Phase A was increased and vigorous mixing was initiated by the double motion impeller. Phase B was slowly added to Phase A, and the mixture was allowed to emulsify for 15–20 minutes. The mixing conditions were maintained until the mixture was cooled to about 50° C.

In the mean time, Phase C was made in a separate smaller vessel by first mixing water and propylene glycol of Phase C. Mixing was continued and sulfur was dispersed. This pre-mix was homogenized for 4–8 minutes using a suitable homogenizer.

This sulfur dispersion was added to the mixture of Phase A and Phase B at 40° C. The combined phases were mixed and cooled to below about 35° C., and ordenone and the other fragrance were added The pH of the mixture was then adjusted to between about 7.7 and 8.11 by the addition of a suitable amount of acid, such as HCl or base, such as NaOH as required. The mixture was cooled to about 30° C. and was then ready for use.

This composition is intended to be used to treat disturbed keratinization, including but not limiting to rosacea (acne rosacea), regular acne (acne vulgaris), and seborrheic dermatitis, as well as microbiologic, viral or parasitic conditions. The composition is preferably applied to human skin once or twice daily and is left on the skin.

Samples of the lotion were prepared as described above. A reference sample was prepared with a pH of about 7.7 to about 8.1. Additional samples were prepared with pH values ranging from 5.0 to 9.5. A portion of each sample, including the reference sample, was stored at 40° C. for two weeks to simulate a longer aging period.

After the two-week aging period, the samples were presented in a blind test to three individual testers who compared the smell of each sample to the corresponding reference sample. The testers rated the degree of difference in smell between the reference sample and the reformulated, pH adjusted, sample on a scale of 0 to 5 as follows:

0=no difference from reference
1=very slight difference from reference
2=slight difference from reference
3=moderate difference from reference
4=considerable difference from reference
5=large difference from reference Note that the difference from reference, if any, represents only a stronger sulfur smell and never a weaker sulfur smell. Thus, the greater the degree of difference between the reference and the comparison sample, the worse smelling the comparison sample and the further the comparison sample was from ideal. It should be noted that this malodor detection test, while commonly relied upon in the art, is subjective and that individual testers may have different sensitivities to these widely and generally perceived sulfurous odors.

The results of this smell test are presented in the following table.

| SULFUR & SODIUM SULFACETAMIDE LOTION | | | | | | |
|---|---|---|---|---|---|---|
| | Tester 1 | | Tester 2 | | Tester 3 | |
| pH | RT | 40° C. | RT | 40° C. | RT | 40° C. |
| 5.5 | N/A | 0 | N/A | 1–2 | N/A | 1 |
| 6.0 | N/A | 1 | N/A | 1 | N/A | 1 |
| 6.5 | N/A | 1–2 | N/A | 0 | N/A | 1 |
| 7.0 | N/A | 1–2 | N/A | 0 | N/A | 1 |
| 7.7–8.1 (reference) | N/A | 0 | N/A | 0 | N/A | 0 |
| 8.5 | N/A | 1–2 | N/A | 2 | N/A | 2 |
| 9.0 | N/A | 1–2 | N/A | 2 | N/A | 2–3 |
| 9.6 | N/A | 2 | N/A | 2 | N/A | 3 |

EXAMPLE 2

A sulfur containing mask composition was prepared by combining the components set forth below in accordance with the procedure set forth below.

| | % by Weight |
|---|---|
| Phase A | |
| Xanthan gum | 0.30 |
| Magnesium aluminum silicate | 1.50 |
| Purified water, USP | q.s. |
| Phase B | |
| Sulfacetamide sodium | 10.00 |
| Kaolin | 18.00 |
| Silica | 5.00 |
| Sodium thiosulfate | 0.10 |

| | % by Weight |
|---|---|
| Phase C | |
| Glyceryl stearate and PEG-100 stearate | 10.00 |
| Benzyl alcohol | 1.00 |
| Quillai extract | 1.00 |
| Phase D | |
| Sulfur precipitated, USP | 5.00 |
| Phase E | |
| Witch hazel | 5.00 |
| Fragrance 27160 | 0.05 |

The water of Phase A was first placed in a suitable-sized kettle equipped with a Lightnin® type mixer and a double motion impeller. The Lightnin® mixer was started to provide fairly vigorous stirring, and the water was heated to about 60–65° C. In a separate vessel xanthan gum and magnesium aluminum silicate were dry-blended. This dry-blended gum was slowly sprinkled into the vortex of the mixing water and the mixing was continued to form a thick, lump-free dispersion. The temperature and mixing conditions were maintained for about 1 hour.

In a separate vessel the powders of Phase B were pre-blended.

In the kettle containing Phase A, the double motion impeller was initiated to start slow mixing. Phase B was added to Phase A. The temperature and mixing conditions were maintained.

In a separate smaller kettle, all of the ingredients of Phase C were loaded and heated to about 65–70° C. Slow mixing was initiated as the solids melt. When all solids were melt, add Phase C to the combined Phase A and Phase B. The combined Phases A, B and C were mixed and cooled to below about 50° C., and the sulfur of Phase D was added. The combined Phases A, B, C and D were mixed and cooled to below about 40° C., and Phase E ingredients were added. The combined phases were mixed and cooled to below about 30° C. and was then ready for use.

The composition is intended to be used to treat disturbed keratinization, including but not limiting to rosacea (acne rosacea), regular acne (acne vulgaris), and seborrheic dermatitis. The composition is preferably applied to human skin and is left on the skin for a moderate amount of time; often for 15 to 60 minutes before being rinsed off. While on the skin, the composition is believed to absorb excess oil, sloughed cells, live and dead microorganisms and mites and their endotoxins and exotoxins; all of which may be irritants that may help provoke the itching, redness and irritation that are characteristics of rosacea. After rinsing, residual sulfur and sodium sulfacetamide are believed to cause residual anti-microbial, anti-fungal, and anti-parasitic activities to inhibit microbial growth and suppress endogenous parasites such as mites.

Samples of the mask composition were prepared as described above. A reference sample was prepared with a pH of about 7.3 to about 7.7. Additional samples were prepared with pH values ranging from 5.0 to 9.6. A portion of each sample, including the reference sample, was stored at room temperature ("RT") for two weeks. The practice of storing samples at elevated temperatures is a widely used method of testing for the persistence of odor reduction and for detecting any tendency for malodors to develop during a product's expected shelf life. The samples were then subjected to the smell test described above with respect to Example 1. The results are presented in the following table.

SULFUR & SODIUM SULFACETAMIDE MASK

| PH | Tester 1 RT | Tester 1 40° C. | Tester 2 RT | Tester 2 40° C. | Tester 3 RT | Tester 3 40° C. |
|---|---|---|---|---|---|---|
| 5.0 | 0 | 0 | 2 | 2 | 2–3 | 4 |
| 5.5 | 1 | 0 | 3 | 3 | 2–3 | 4 |
| 6.0 | 1 | 0 | 1 | 1 | 1 | 2 |
| 6.5 | 1–2 | 1 | 0–1 | 0–1 | 1–2 | 1 |
| 7.0 | 1–2 | 1 | 0 | 0 | 3 | 2 |
| 7.3 to 7.7 (reference) | — | 0 | — | 0 | — | 0 |
| 8.0 | 1 | 1 | 1 | 1 | 2–3 | 2–3 |
| 8.5 | 1–2 | 1–2 | 1–2 | 1–2 | 2–3 | 3 |
| 9.0 | 1–2 | 1 | 1–2 | 1–2 | 3 | 2–3 |
| 9.6 | 1–2 | 1–2 | 2 | 2 | 4 | 4 |

EXAMPLE 3

A sulfur containing cleanser composition was prepared by combining the components set forth below in accordance with the procedure set forth below.

| | % by Weight |
|---|---|
| Phase A | |
| Sodium methyl oleyltaurate | 9.00 |
| Disodium oleamido MEA sulfosuccinate | 5.00 |
| PEG-55 propylene glycol oleate | 0.80 |
| Phase B | |
| Sodium cocoyl isethionate | 8.50 |
| Methylparaben | 0.15 |
| Propylparaben | 0.05 |
| $Na_2EDTA$ | 0.10 |
| BHT | 0.10 |
| Purified water, USP | q.s. |
| Phase C | |
| Cetyl alcohol, NF | 3.50 |
| Stearyl alcohol, NF | 1.50 |
| Sorbitan stearate | 0.50 |
| Glyceryl stearate and PEG-100 stearate | 2.50 |
| Phase D | |
| Sulfacetamide sodium, USP | 10.00 |
| Sodium thiosulfate | 0.10 |
| Phase E | |
| Sulfur precipitated, USP | 5.00 |
| Magnesium aluminum silicate | 0.40 |
| Xanthan gum | 0.08 |
| Purified water | 7.52 |
| Phase F | |
| Fragrance 27160 | 0.10 |

To make the composition, the ingredients of Phase A were loaded into a suitable-sized kettle equipped with a double motion impeller. The ingredients were heated to about 45–55° C. and were mixed and completely melted.

In a separate smaller kettle equipped with a Lightnin type mixer, the water of Phase B was added and while being mixed at moderate speed, was heated to about 60–65° C. Sodium cocoyl isethionate was added to the mixing water and was completely dissolved. Then the rest of the ingredients of Phase B were added and were completely dissolved.

Phase A and Phase B were combined and heated to about 70–75° C.

In a separate suitable-sized kettle, Phase C ingredients were added and heated to about 70–75° C. When all ingredients were melted, Phase C was added to the combined Phase A and Phase B. While the temperature and mixing conditions were maintained, the ingredients of Phase D were added one by one into the combined phases A, B and C.

In a separate vessel, the water of Phase E was mixed to create a vortex and was heated. In another separate vessel, xanthan gum and magnesium aluminum silicate were dry-blended. This dry-blended gum was sprinkled into the vortex of Phase E water and was mixed to form a thick, lump-free dispersion. While continuing mixing, the sulfur was added to the gum dispersion and was mixed to obtain a smooth suspension.

The sulfur suspension formed by Phase E ingredients was added to the combined phases A, B, C and D and was mixed and cooled to below about 40° C. Fragrance of Phase F was then added to the combined phases A, B, C, D and E and was mixed. The mixture was cooled to below about 30° C. and was ready for use.

The cleanser is intended to be used to treat disturbed keratinization, including but not limiting to rosacea (acne rosacea), regular acne (acne vulgaris), and seborrheic dermatitis as well as microbiologic, viral or parasitic conditions. The composition is preferably applied to the skin and is usually massaged into the surface of the skin, often with added water for a few minutes before being rinsed off. While on the skin and during its' removal, it is believed to removes the excess oil, sloughed cells, live and dead microorganisms and mites with their endotoxins and exotoxins; all of which can be irritants that may contribute to the provocation of the itching, redness and irritation that are characteristics of rosacea.

Cleanser compositions according to the present inventions are remarkably effective in the treatment of acne roseacea, and yield results that are significantly better than expected. These superior results include more rapid and further reduction of the erythema, puritis, burning or stinging, and even mite infestations sometimes associated with this condition.

Samples of the cleanser were prepared as described above. A reference sample was prepared with a pH of about 7.0 to about 7.1. Additional samples were prepared with pH values ranging from 5.0 to 9.5. A portion of each sample, including the reference sample, was stored at 40° C. for two weeks. The samples were then subjected to the smell test described above with respect to Example 1. The results are presented in the following table.

SULFUR & SODIUM SULFACETAMIDE CLEANSER

| PH | Tester 1 RT | Tester 1 40° C. | Tester 2 RT | Tester 2 40° C. | Tester 3 RT | Tester 3 40° C. |
|---|---|---|---|---|---|---|
| 5.0 | N/A | 1 | N/A | 1 | N/A | 1 |
| 5.5 | N/A | 1 | N/A | 1 | N/A | 1 |
| 6.0 | N/A | 0 | N/A | 1 | N/A | 1 |
| 7.0–7.11 (reference) | N/A | 0 | N/A | 0 | N/A | 0 |
| 7.5 | N/A | 1 | N/A | 1–2 | N/A | 1–2 |
| 8.0 | N/A | 1 | N/A | 1–2 | N/A | 2 |
| 8.6 | N/A | 1 | N/A | 2 | N/A | 2 |
| 9.0 | N/A | 1 | N/A | 2–3 | N/A | 2 |
| 9.5 | N/A | 1 | N/A | 2–3 | N/A | 2–3 |

It will be understood by persons of ordinary skill in the art that various changes in the details, compositions, steps and arrangements of the components and steps which have been described and illustrated to explain the nature of this invention may be made by those skilled in the art without departing from the principle and scope of the invention as expressed in the following claims.

What is the claimed is:

1. A composition suitable for topical application to human skin or hair, comprising:

Sulfur at about 5% by weight;

Sodium sulfacetamide at about 10% by weight; and a pharmaceutically acceptable carrier; wherein the carrier is a cleanser and the composition has a pH of from about 6.5 to about 8.1.

2. The composition of claim 1 wherein the pH of the composition is from about 7.0 to about 8.1.

3. The composition of claim 1 wherein the composition has a pH of about 7.3 to about 7.7.

4. The composition as in one of claims 1, 2, or 3 further comprising one or more of the group consisting of an antimicrobial agent, an antifungal agent, an anti-inflammatory agent, an immunomodulator, an immunosuppressant, an antiparasitic agent, a keratinization modulator, a depigmenting agent, an antihistamine, and an antioxidant.

5. The composition of claim 1 further comprising xanthan gum, disodium EDTA, sodium thiosulfate, water, mineral oil, isopropyl myristate, stearyl alcohol, cetyl alcohol, hydrogenated coco-glycerides, benzyl alcohol, zinc ricinoleate, sorbitan stearate, dimethicone, polysorbate 60, glyceryl stearate and PEG-100 stearate, propylene glycol, and ordenone.

6. The composition of claim 1 further comprising xanthan gum, magnesium aluminum silicate, water, kaolin, silica, sodium thiosulfate, glyceryl stearate and PEG-100 stearate, benzyl alcohol, quillai extract, and witch hazel.

7. The composition of claim 1 further comprising disodium oleamido MEA sulfosuccinate, sodium methyl oleyltaurate, PEG-55 propylene glycol oleate, sodium cocoyl isethionate, methylparaben, propylparaben, Na$_2$EDTA, BHT, water, cetyl alcohol, stearyl alcohol, sorbitan stearate, glyceryl stearate and PEG-100 stearate, sodium thiosulfate, magnesium aluminum silicate, and xanthan gum.

8. A composition suitable for topical application to human skin or hair, comprising:

a. sulfur at about 5% by weight and sodium sulfacetamide at about 10% by weight; and b. a pharmaceutically acceptable carrier;
      wherein the carrier is a cleanser, the composition has a pH of from about 6.5 to about 8.1 and the composition exhibits substantially reduced sulfur odor.

9. The composition of claim 8, wherein the composition exhibits substantially reduced sulfur odor after aging.

10. The composition of claim 8 wherein the pH of the composition is from about 7.0 to about 8.1.

11. The composition of claim 8 wherein the carrier is a cleanser and the composition has a pH of from about 7.0 to about 7.1.

12. The composition of claim 8 further comprising xanthan gum, disodium EDTA, sodium thiosulfate, water, mineral oil, isopropyl myristate, stearyl alcohol, cetyl alcohol, hydrogenated coco-glycerides, benzyl alcohol, zinc ricinoleate, sorbitan stearate, dimethicone, polysorbate 60, glyceryl stearate and PEG-100 stearate, propylene glycol, and ordenone.

13. The composition of claim 8 further comprising xanthan gum, magnesium aluminum silicate, water, kaolin, silica, sodium thiosulfate, glyceryl stearate and PEG-100 stearate, benzyl alcohol quillai extract, and witch hazel.

14. The composition of claim 8 further comprising disodium oleamido MEA sulfosuccinate, sodium methyl oleyltaurate, PEG-55 propylene glycol oleate, sodium cocoyl isethionate, methylparaben, propylparaben, Na$_2$EDTA, BHT, water, cetyl alcohol, stearyl alcohol, sorbitan stearate, glyceryl stearate and PEG-100 stearate, sodium thiosulfate, magnesium aluminum silicate, and xanthan gum.

15. A composition for treating acne rosacea comprising:

a. sulfur at about 5% by weight and sodium sulfacetamide at about 10% by weight; and b. a pharmaceutically acceptable carrier, wherein the carrier is a cleanser.

16. A method for treating acne rosacea comprising the step of applying to the skin of a user a composition comprising sulfur at about 5% by weight and sodium sulfacetamide at about 10% by weight and a pharmaceutically acceptable carrier, wherein the carrier is a cleanser.

17. A composition for treating acne rosacea comprising:

sulfur at about 5% by weight and sodium sulfacetamide at about 10% by weight; and a pharmaceutically acceptable carrier, wherein the carrier is a cleanser, and the composition has a pH of from about 6.5 to about 8.1.

18. The composition of claim 17 wherein the pH of the composition is from about 7.0 to about 8.1.

19. The composition of claim 17 wherein the carrier comprises a cleanser and the composition has a pH of about 7.3 to about 7.7.

20. The compositions as in one of claim 17, 18, 19 further comprising one or more of the group consisting of an antimicrobial agent, an antifungal agent, an anti-inflammatory agent, an immunomodulator, an immunosuppressant, an antiparasitic agent, a keratinization modulator, a depigmenting agent, an antihistamine, and an antioxidant.

21. The composition of claim 17 further comprising sodium methyl oleylaurate, disodium oleamido MEA sulfosuccinate, PEG-55 propylene glycol oleate, water, sodium cocoyl isethionate, methyl paraben, propyl paraben, disodium EDTA, cetyl alcohol, stearyl alcohol, glyceryl stearate, PEG-100 stearate, BHT, sodium thiosulfate, magnesium aluminum silicate, and xanthan gum.

22. The composition of claim 17 further comprising water, propylene glycol, isopropyl myristate, mineral oil, polysorbate 60, sorbitan monostearate, cetyl alcohol, hydrogenated coco-glycerides, stearyl alcohol, ordenone, benzyl alcohol, glyceryl stearate, PEG-100 stearate, zinc ricinoleate, dimethicone, xanthan gum, disodium EDTA, and sodium thiosulfate.

23. A method for treating acne rosacea comprising applying to the skin of a user a composition comprising sulfur at about 5% by weight, sodium sulfacetamide at about 10% by weight and a pharmaceutically acceptable carrier; wherein the carrier is a cleanser and the composition has a pH of from about 6.5 to about 8.1.

24. The method of claim 23 wherein the pH of the composition is from about 7.0 to about 8.1.

25. The method of claim 23 wherein the composition has a pH of about 7.3 to about 7.7.

26. The methods as in one of claims 23, 24, 25 wherein the composition further comprises one or more of the group consisting of an antimicrobial agent, an antifungal agent, an anti-inflammatory agent, an immunomodulator, an immunosuppressant, an antiparasitic agent, a keratinization modulator, a depigmenting agent, an antihistamine, and an antioxidant.

27. The method of claim 23 wherein the composition further comprises sodium methyl oleylaurate, disodium oleamido MBA sulfosuccinate, PEG-55 propylene glycol oleate, water, sodium cocoyl isethionate, methyl paraben, propyl paraben, disodium EDTA, cetyl alcohol, stearyl alcohol, glyceryl stearate, PEG-100 stearate, BHT, sodium thiosulfate, magnesium aluminum silicate, and xanthan gum.

28. The method of claim 23 wherein the composition further comprises water, propylene glycol, isopropyl myristate, mineral oil, polysorbate 60, sorbitan monostearate, cetyl alcohol, hydrogenated coco-glycerides, stearyl alcohol, ordenone, benzyl alcohol, glyceryl stearate, PEG-100 stearate, zinc ricinoleate, dimethicone, xanthan gum, disodium EDTA, and sodium thiosulfate.

* * * * *

UNITED STATES PATENT AND TRADEMARK OFFICE
CERTIFICATE OF CORRECTION

PATENT NO. : 6,905,675 B2
DATED : June 14, 2005
INVENTOR(S) : Shacknai et al.

It is certified that error appears in the above-identified patent and that said Letters Patent is hereby corrected as shown below:

Column 1,
Line 11, "The present invention related methods of reducing" should read as -- The present invention relates to methods of reducing --.
Line 43, "apply such compositions directed" should read as -- apply such compositions as directed --.

Column 5,
Line 5, "ascorbic acid and ets" should read as -- ascorbic acid and its --.

Column 13,
Line 8, "MBA" should read as -- MEA --.

Signed and Sealed this

Sixteenth Day of August, 2005

JON W. DUDAS
*Director of the United States Patent and Trademark Office*

(12) EX PARTE REEXAMINATION CERTIFICATE (7625th)
United States Patent
Shacknai et al.

(10) Number: US 6,905,675 C1
(45) Certificate Issued: *Jul. 20, 2010

(54) SULFUR CONTAINING DERMATOLOGICAL COMPOSITIONS AND METHODS FOR REDUCING MALODORS IN DERMATOLOGICAL COMPOSITIONS

(75) Inventors: Jonah Shacknai, Scottsdale, AZ (US); Eugene H. Gans, Phoenix, AZ (US); Ray Figureoa, Medley, FL (US)

(73) Assignee: Medicis Pharmaceutical Corporation, Scottsdale, AZ (US)

Reexamination Request:
No. 90/008,068, Jun. 16, 2006

Reexamination Certificate for:
Patent No.: 6,905,675
Issued: Jun. 14, 2005
Appl. No.: 10/283,102
Filed: Oct. 29, 2002

(*) Notice: This patent is subject to a terminal disclaimer.

Certificate of Correction issued Aug. 16, 2005.

Related U.S. Application Data

(63) Continuation of application No. 09/607,881, filed on Jun. 30, 2000, now Pat. No. 6,514,489.

(51) Int. Cl.
*A61K 47/02* (2006.01)
*A61K 47/36* (2006.01)
*A61K 47/12* (2006.01)
*A61K 47/00* (2006.01)
*A61K 47/24* (2006.01)
*A61K 47/14* (2006.01)
*A61K 47/10* (2006.01)
*A61K 8/25* (2006.01)
*A61K 8/23* (2006.01)
*A61K 8/26* (2006.01)
*A61K 8/19* (2006.01)
*A61K 31/63* (2006.01)
*A61K 33/04* (2006.01)
*A61K 8/46* (2006.01)
*A61K 8/30* (2006.01);
*A61Q 19/00* (2006.01)

(52) U.S. Cl. .......... 424/70.1; 424/401; 424/703; 424/705; 424/706; 514/613; 514/886; 514/887

(58) Field of Classification Search .......... None
See application file for complete search history.

(56) References Cited

U.S. PATENT DOCUMENTS 5,330,980 A  7/1994  Shin
5,445,823 A  8/1995  Hall et al.
6,429,231 B1  8/2002  Bhagwat et al.
2002/0164381 A1  11/2002  Shacknai et al.

OTHER PUBLICATIONS

Skin Basics—Cetaphil. 2002.*
The Merck Index (1976). Ninth Edition. p. 14.
Cetaphil Canada, Product Information.
European Patent Office, Supplementary European Search Report , Sep. 1, 2006.
Sauder, D. et al., "The Treatment of Rosacea: The Safety and Efficacy of Sodium Sulfacetamide 10% and Sulfer 5% Lotion (Novacet) is Demonstrated in a Double–Blind Study," Journal of Dermatological Treatment, Basingstoke, Great Britain, vol. 8, No. 2, Jun. 1997, (1997–08), pp.79–85.
Database WPI, Section Ch, Week 198606, Derwent Publications Lyd., London, Great Britain, AN 81986–040399, XP002396723 & RO 87 009 A (Intr Prod Cosmetice Farmec) May 3, 1985 (abstract).
Modern Soap And Detergent Industry, Martin, Chap. IV, p. 20–40, 1932.
Cosmetic Dermatology: H. Goodman 1936, p. 199, 201, 211, 478–479, 481.
Soaps and Detergents, 1949,p. 7–9, 250–331, 473–511.
A.M.A. Archives of Dermatology and Syphilogy: Jul. 1954, p. 75–82.
American Perfumer, vol. 77, No. 1, Jan. 1962, p. 27–32.
Acne and Related Disorders, A. Bobroff, 1964.
Virginia Medical Monthly, vol. 93, Feb. 1966, p. 78–79.
Chemical Stability of Pharmaceuticals, 1979,p. 311–317.
Sulfacet pH measurements (email to Dr. Gans, Dec. 17, 2003).
International Journal of Dermatology, vol. 32, No. 5, May 1993, p. 365–367.
Journal of Clinical Pharmacy and Therapeutics, vol. 22, No. 4, Aug. 1997, p. 300–303.
PDR, Ed. 31, 1977, p. 1587.
PDR, Ed. 47, 1993, p. 934–935.
PDR, Ed. 48, 1994, p. 998–999.
PDR, Ed. 52, 1998, p. 982.
PDR, Ed. 53, 1999, p. 1717.
Clinical Medicine, May 1960, vol. 7, No. 5, p. 991–994.

* cited by examiner

*Primary Examiner*—Evelyn Huang

(57) ABSTRACT

A method for reducing the production of malodor in sulfur containing dermatological compositions by adjusting the pH of the composition to between about 6.5 to about 8.1. Also, sulfur containing dermatological compositions having a pH between about 6.5 and about 8.1.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 27-28 is confirmed.

Claims 1-4, 8-11, 15-20 and 23-26 are cancelled.

Claims 5-7, 12-14, 21 and 22 are determined to be patentable as amended.

5. [The] *A* composition [of claim 1] *suitable for topical application to human skin or hair, comprising: Sulfur at about 5% by weight; Sodium sulfacetamide at about 10% by weight; and a pharmaceutically acceptable carrier; wherein the carrier is a cleanser and the composition has a pH of from about 6.5 to about 8.1, and* further comprising xanthan gum, disodium EDTA, sodium thiosulfate, water, mineral oil, isopropyl myristate, stearyl alcohol, cetyl alcohol, hydrogenated cocogylcerides, benzyl alcohol, zinc ricinoleate, sorbitan stearate, dimethicone, polysorbate 60, glyceryl stearate and PEG-100 stearate, propylene glycol, and ordenone.

6. [The] *A* composition [of claim 1] *suitable for topical application to human skin or hair, comprising: Sulfur at about 5% by weight; Sodium sulfacetamide at about 10% by weight; and a pharmaceutically acceptable carrier; wherein the carrier is a cleanser and the composition has a pH of from about 6.5 to about 8.1 and* further comprising xanthan gum, magnesium aluminum silicate, water, kaolin, silica, sodium thiosulfate, glyceryl stearate and PEG-100 stearate, benzyl alcohol, quillai extract, and witch hazel.

7. [The] *A* composition [of claim 1] *suitable for topical application to human skin or hair, comprising: Sulfur at about 5% by weight; Sodium sulfacetamide at about 10% by weight; and a pharmaceutically acceptable carrier; wherein the carrier is a cleanser and the composition has a pH of from about 6.5 to about 8.1 and* further comprising disodium oleamido MEA sulfosuccinate, sodium methyl oleyltaurate, PEG-55 propylene glycol oleate, sodium cocoyl isethionate, methylparaben, propylparaben, Na$_2$EDTA, BHT, water, cetyl alcohol, stearyl alcohol, sorbitan stearate, glyceryl stearate and PEG-100 stearate, sodium thiosulfate, magnesium aluminum silicate, and xanthan gum.

12. [The composition of claim 8] *A composition suitable for topical application to human skin or hair, comprising:*
a. *sulfur at about 5% by weight and sodium sulfacetamide at about 10% by weight; and*
b. *a pharmaceutically acceptable carrier; wherein the carrier is a cleanser, the composition has a pH of from about 6.5 to about 8.1 and the composition exhibits substantially reduced sulfur odor, and* further comprising xanthan gum, disodium EDTA, sodium thiosulfate, water, mineral oil, isopropyl myristate, stearyl alcohol, cetyl alcohol, hydrogenated coco-glycerides, benzyl alcohol, zinc ricinoleate, sorbitan stearate, dimethicone, polysorbate 60, glyceryl stearate and PEG-100 stearate, propylene glycol, and ordenone.

13. [The composition of claim 8] *A composition suitable for topical application to human skin or hair, comprising:*
a. *sulfur at about 5% by weight and sodium sulfacetamide at about 10% by weight; and*
b. *a pharmaceutically acceptable carrier; wherein the carrier is a cleanser, the composition has a pH of from about 6.5 to about 8.1 and the composition exhibits substantially reduced sulfur odor, and* further comprising xanthan gum, magnesium aluminum silicate, water, kaolin, silica, sodium thiosulfate, glyceryl stearate and PEG-100 stearate, benzyl alcohol quillai extract, and witch hazel.

14. [The composition of claim 8] *A composition suitable for topical application to human skin or hair, comprising:*
a. *sulfur at about 5% by weight and sodium sulfacetamide at about 10% by weight; and*
b. *a pharmaceutically acceptable carrier; wherein the carrier is a cleanser, the composition has a pH of from about 6.5 to about 8.1 and the composition exhibits substantially reduced sulfur odor, and* further comprising disodium oleamido MEA sulfosuccinate, sodium methyl oleyltaurate, PEG-55 propylene glycol oleate, sodium cocoyl isethionate, methylparaben, propylparaben, Na$_2$EDTA, BHT, water, cetyl alcohol, stearyl alcohol, sorbitan stearate, glyceryl stearate and PEG-100 stearate, sodium thiosulfate, magnesium aluminum silicate, and xanthan gum.

21. [The composition of claim 17] *A composition for treating acne rosacea comprising: sulfur at about 5% by weight and sodium sulfacetamide at about 10% by weight; and*

*a pharmaceutically acceptable carrier, wherein the carrier is a cleanser, and the composition has a pH of from about 6.5 to about 8.1 and* further comprising sodium methyl oleylaurate, disodium oleamido MEA sulfosuccinate, PEG-55 propylene glycol oleate, water, sodium cocoyl isethionate, methyl paraben, propyl paraben, disodium EDTA, cetyl alcohol, stearyl alcohol, glyceryl stearate, PEG-100 stearate, BHT, sodium thiosulfate, magnesium aluminum silicate, and xanthan gum.

22. [The composition of claim 17] *A composition for treating acne rosacea comprising: sulfur at about 5% by weight and sodium sulfacetamide at about 10% by weight; and*

*a pharmaceutically acceptable carrier, wherein the carrier is a cleanser, and the composition has a pH of from about 6.5 to about 8.1 and* further comprising water, propylene glycol, isopropyl myristate, mineral oil, polysorbate 60, sorbitan monostearate, cetyl alcohol, hydrogenated coco-glycerides, stearyl alcohol, ordenone, benzyl alcohol, glyceryl stearate, PEG-100 stearate, zinc ricinoleate, dimethicone, xanthan gum, disodium EDTA, and sodium thiosulfate.

* * * * *